(12) United States Patent
Meléndez et al.

(10) Patent No.: US 8,747,427 B2
(45) Date of Patent: Jun. 10, 2014

(54) AUTOMATED DELIVERY OF FLUID

(75) Inventors: Tomás Meléndez, San Jose, CA (US); Clifford A. Oostman, Jr., Hansville, WA (US); Brian E. Tippett, San Antonio, TX (US)

(73) Assignee: Restoration Robotics, Inc., San Jose, CA (US)

( * ) Notice: Subject to any disclaimer, the term of this patent is extended or adjusted under 35 U.S.C. 154(b) by 159 days.

(21) Appl. No.: 13/008,248

(22) Filed: Jan. 18, 2011

(65) Prior Publication Data

US 2012/0184969 A1 Jul. 19, 2012

(51) Int. Cl.
*A61B 17/34* (2006.01)

(52) U.S. Cl.
USPC ............................................. 606/185; 604/65

(58) Field of Classification Search
USPC ................ 606/130, 187; 600/574; 604/65, 67
See application file for complete search history.

(56) References Cited

U.S. PATENT DOCUMENTS

| | | | |
|---|---|---|---|
| 2,845,068 A | 3/1953 | Gabriel | |
| 2,879,766 A | 7/1955 | Wilburn | |
| 4,142,525 A | 3/1979 | Binard et al. | |
| 4,230,111 A | 10/1980 | Piazza et al. | |
| 4,343,306 A | 8/1982 | Mericle | |
| 5,409,477 A * | 4/1995 | Caron et al. | 604/407 |
| 5,489,265 A * | 2/1996 | Montalvo et al. | 604/67 |
| 5,968,282 A | 10/1999 | Yamasaka | |
| 6,585,746 B2 | 7/2003 | Gildenberg | |
| 6,775,879 B2 | 8/2004 | Bibeault et al. | |
| 7,487,800 B2 | 2/2009 | Lammers | |
| 7,621,934 B2 * | 11/2009 | Bodduluri et al. | 606/187 |
| 2003/0168082 A1 | 9/2003 | Cundith et al. | |
| 2005/0085838 A1 | 4/2005 | Thompson et al. | |
| 2007/0106306 A1 | 5/2007 | Bodduluri et al. | |
| 2008/0177287 A1 | 7/2008 | Rassman et al. | |
| 2009/0012536 A1 | 1/2009 | Rassman et al. | |
| 2009/0326480 A1* | 12/2009 | Milijasevic | 604/246 |
| 2012/0165832 A1 | 6/2012 | Oostman, Jr. et al. | |

OTHER PUBLICATIONS

PCT International Search Report, Form PCT/ISA/210, mailed Aug. 14, 2012, 4 pages.
PCT International Preliminary Report on Patentability, Forms PCT/IB/326, PCT/IB/373 and PCT/ISA/237, mailed Aug. 1, 2013, (9 pages).

* cited by examiner

*Primary Examiner* — Victor Nguyen
(74) *Attorney, Agent, or Firm* — Lena I. Vinitskaya; Sharon Upham

(57) ABSTRACT

The present application is directed to apparatus, systems and methods for automated delivery of fluids. According to one aspect, it is especially useful in providing a restricted flow of fluid to a tool, for example, a cannula or a needle used in hair transplantation. According to another aspect, the systems and methods provided herein enable the hair harvesting or a hair implantation tool to be cleaned, flushed or lubricated.

25 Claims, 4 Drawing Sheets

AUTOMATED DELIVERY OF FLUID

FIELD OF THE INVENTION

This invention relates generally to delivery of fluid to the needles or cannulas, and in particular, to automated fluid delivery apparatus, systems and methods.

BACKGROUND OF THE INVENTION

There are various medical and cosmetic procedures that may be performed now using various degrees of automation, in some instances using hand-held automated tools, in other instances utilizing automated systems that may include robotic arms, for example. No matter what the level of automation, it is important that the user ensures that the cannula or needles are maintained at the required level of cleanliness, so that they do not contribute to infections or other such contamination issues of the patient or associated equipment. One such medical procedure is hair transplantation. Hair transplantation is a highly repetitive, time consuming and tedious procedure that can last many hours (e.g. whole day), and therefore the development of an image-guided robotic system for follicular unit extraction and implantation has been proposed, for example, in the commonly-assigned U.S. Patent Publication No. 2007/0106306 to Bodduluri et al. The Bodduluri et al. '306 publication discloses a robotic system for harvesting and/or implanting FUs having a robotic arm and a tool (e.g. harvesting cannula or punch) operatively attached to the robotic arm. A robotic arm is positioned relative to a patient, so that a targeted body surface (in this instance, the donor area on the back of a patient's scalp) is within reach of a harvesting or implanting tool. The robotic system may include one or more cameras, and a processor receives and processes the images acquired thereby. A controller operatively associated with the processor precisely maneuvers the robotic arm to position the tool at desired locations and in desired orientations, for example, relative to follicular units targeted for harvesting from the scalp or at the desired implantation locations and orientations.

SUMMARY OF THE INVENTION

In accordance to one general aspect, the present application discloses apparatus, systems and methods that could be used to automatically dispense fluid to a tool, for example, a harvesting tool or implanting tool used in a hair transplantation procedure. According to one aspect, an apparatus for dispensing fluid is provided. The apparatus comprises an adapter that may be configured to restrict fluid delivery, for example, a volume or an amount of fluid provided or delivered to a tool. In some embodiments, the adapter may include a first opening configured to receive a distal end of the tool, a second opening configured to receive fluid from a fluid dispenser; and a pathway disposed between the first opening and the second opening, the pathway configured to restrict a flow of fluid from the second opening to the first opening. The apparatus further comprises an actuation mechanism configured to cause fluid delivery to the second opening of the adapter when the distal end of the tool is disposed or positioned within or at the first opening of the adapter. In some embodiments, the above apparatus may be a part of the automated system, such as robotic system, and may further comprise the tool (e.g. harvesting tool). In further embodiments, the actuation mechanism may be configured to be actuated by a pressure differential. The apparatus may further comprise one or more sensors for sensing, for example, presence of the tool within or at the first opening.

In other embodiments a first opening of the adapter may be connected to tubing or other intermediate connector through which fluid may be eventually delivered to the tool. An apparatus comprising an adapter configured to restrict fluid delivery to a tool may also include in various embodiments a computer or a processor programmed, for example, to actuate an actuation mechanism such that fluid is caused to be delivered to an adapter.

According to another aspect, a robotic system, such as hair transplantation system is provided, the system including a robotic arm with a tool, such as a hair transplantation tool, attached thereto. In one embodiment, the robotic system is situated on a cart, and the cart is configured to also accommodate a fluid dispensing apparatus or system. In another embodiment, the fluid dispensing apparatus may be positioned on the robotic arm, or the tool assembly, or other appropriate location. Such fluid dispensing apparatus may comprise a fluid dispensing adapter of the present application. The robotic system may be configured to move the robotic arm and/or the hair transplantation tool to substantially align a distal end of the tool with an opening in the fluid dispensing adapter. When the distal end of the tool is so aligned, an actuation mechanism, which may be computer controlled, actuates fluid delivery through the fluid dispensing adapter to the tool.

In yet another aspect, methods for automatically dispensing fluid are provided. According to one example of the embodiment of the method, the method may comprise positioning a distal end of a tool within or at a first opening of an adapter; actuating an actuation mechanism to cause fluid to be dispensed from a fluid dispenser and into a second opening of the adapter; and restricting the flow of fluid along a pathway from the second opening to the first opening of the adapter. In same embodiments positioning the distal end of the tool at the first opening of the adapter actuates the actuation mechanism. In another embodiments or implementations of the method, a distal end of the tool does not need to be connected to the adapter. Instead, the tool may be operatively connected, for example, to tubing or a connector that is in turn is coupled to the adapter, and actuation of the fluid delivery may be controlled, for example, by a processor (e.g. computer). In some embodiments image acquisition and processing may be used to determine whether the tool is at a predetermined distance from, or at, or within the adapter to actuate the actuation mechanism. The flow of fluid may be restricted along a pathway using a barrier, and in some embodiments the flow of fluid may be restricted along the pathway by offsetting at least two portions of the pathway.

In another aspect, the present application provides machine-readable media on which are provided program instructions for performing one or more inventive processes or methods described herein. In still another aspect, the present application provides an apparatus comprising a processor configured or designed to perform one or more of the inventive methods.

Other and further objects and advantages of the invention will become apparent from the following detailed description when read in view of the accompanying figures.

BRIEF DESCRIPTION OF THE DRAWINGS

It should be noted that the drawings are not to scale and are intended only as an aid in conjunction with the explanations in the following detailed description. In the drawings, identical reference numbers, if any, identify similar elements or acts. The sizes and relative positions of elements in the drawings are not necessarily drawn to scale. For example, the shapes of various elements and angles are not drawn to scale, and some of these elements may be arbitrarily enlarged and positioned to improve drawing legibility. Features and advantages of the present invention will become appreciated as the same become better understood with reference to the specification, claims, and appended drawings wherein:

DETAILED DESCRIPTION OF THE PREFERRED EMBODIMENTS

Figure 1:
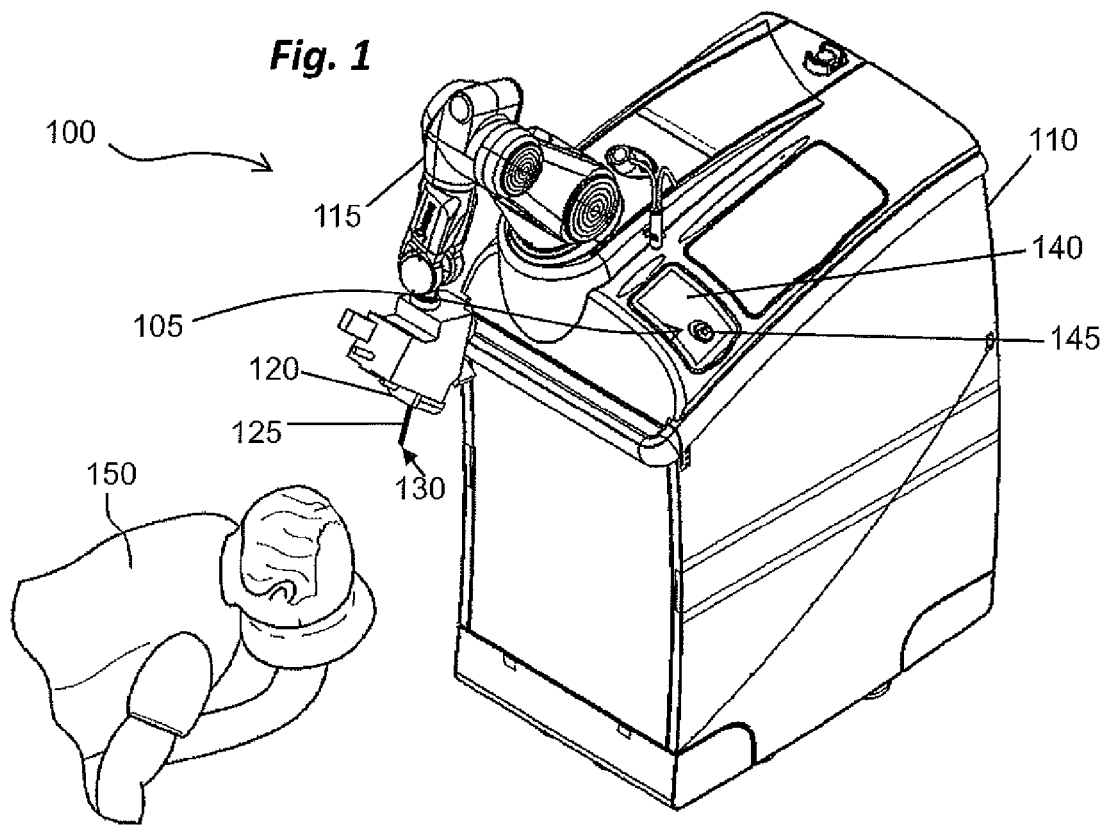
FIG. 1 is a schematic representation of an example of a robotic system that could be implemented in various embodiments of the invention.

In the following Detailed Description, reference is made to the accompanying drawings that show by way of illustration some examples of embodiments in which the invention may be practiced. It is to be understood that other embodiments may be utilized and structural or logical changes may be made without departing from the scope of the invention. In this regard, directional terminology, such as "right", "left", "upwards", "downwards", "inner", "outer", "first", "second" etc., are used with reference to the orientation of the Figure(s) being described. Because components or embodiments of the present invention can be positioned or operated in a number of different orientations, the directional terminology is used for purposes of illustration and is in no way limiting. The terms "operatively connected," "coupled," or "mounted," or "attached" as used herein, means directly or indirectly operatively connected, coupled, attached, or mounted through one or more intervening components. The following description, therefore, is not to be taken in a limiting sense, and the scope of the invention is defined by the appended claims.

The term "tool" as used herein includes, for example, any number of medical (including cosmetic) tools or end effectors that are capable of removing, dissecting, harvesting, implanting or otherwise manipulating various biological tissues, for example, follicular units ("FUs"). Such tools may have many different forms and configurations. In many embodiments, the tool comprises a hollow tubular shaft and thus may be labeled, for example, a cannula, a needle, or a punch. The distal end of tools (for example, punches, coring devices, cutting and/or trimming devices, needles) may be sharpened, for example, to pierce, cut, or extract the tissue (e.g., hair follicle). While various embodiments described herein are explained in reference to hair transplantation, it will be understood that the apparatuses, systems and methods described herein may be implemented in other applications, for example, in dispensing medical glue/adhesive, or dispensing lubrication oil to bearings used in prosthetic devices.

Embodiments of the methods of the invention described herein may be implemented using computer software, firmware or hardware. Various programming languages and operating systems may be used to implement the inventions described herein.

Hair transplantation typically involves hair harvesting and hair implantation (which may include making small holes in a bald area where follicular units will be implanted, sometimes called "site making"). There are various existing methods of performing hair harvesting, including, for example, a strip harvesting and the follicular unit extraction (FUR). In a strip harvesting procedure, the donor tissue (such as a strip of scalp) is removed under local anesthesia, the wound is sutured back together, and the removed piece of scalp tissue is then cut under a microscope into small pieces of tissue called grafts which are subsequently transplanted back into the thinning or bald area. Throughout the manual process, whether it is harvesting or implanting the grafts, the surgeon is able to clean or flush out any of the tools by flowing fluid through them, for example, a saline solution. Since the surgeon is performing the procedure, he or she can elect to clean tools at any point throughout the medical procedure.

Since hair transplantation is a highly repetitive, time consuming and a tedious procedure that could last many hours (e.g. whole day), in addition to hair transplantation procedures performed using manual or hand-held devices, the development of an image-guided robotic system for follicular unit extraction and implantation have been proposed, for example, in the commonly-assigned U.S. Patent Publication No. 2007/0106306, which is incorporated herein by reference. The robotic implementation of any or all parts of the procedure may greatly improve and speed up the overall process, however, it still needs to ensure that needles or cannulas utilized are maintained sufficiently flushed or clean throughout any hair transplantation procedure performed by such a system, or (in reference to hair transplantation procedure) that follicular units remain suitably moistened during the procedure. One solution to this problem is to utilize a supply of fluid (e.g., water, medical glue, lubrication oils, saline or other physiologic fluid), for example, from a saline bag, with a valve, such as pinch valve, configured to limit the amount or volume of saline delivered to the tool. Such a solution will also require using various necessary tubing for transporting the saline from the bag to the tool for delivery of fluid to the tool, for example, to the distal tip of the tool. Use of such a system incorporating the saline bag, various tubes, clips and valves may have a disadvantage of being not cost-efficient. The standard saline bags typically contain about 250 to 1000 cc or ml of saline. Once the saline bag is opened, even since only a small volume of the saline in the bag is used during procedure (typically less than 10 cc of fluid may be required for the entire hair harvesting or hair implantation procedure), the rest of the bag with the remaining solution must be thrown out which may result with some unnecessary waste and expense.

The present application is directed to systems and methods that provide substantially automated delivery of fluid to the distal end of a cannula or needle associated with a robotic system such as the hair transplantation system described above. The systems and methods of the inventions described herein are particularly suited to applications in which it is desirable to deliver a substantially small amount of fluid, for example, just one or a few drops, to a tool such as a needle or cannula. Additionally, the systems and methods described herein may be beneficial in reducing the pressure at which fluid is delivered to tissue, thereby reducing the risk of inadvertent tissue injury. Although the systems and methods of this application are especially useful in hair transplantation procedures, it will be appreciated that they can equally be applied to other applications in which fluid dispensing to the tool (e.g., distal end of the tool) is required. The delivery of fluid may serve, for example, to flush and/or clean the cannula throughout the automated medical procedure. The delivery of fluid to the tool may be also used for lubrication (e.g., to reduce friction between the tool and tissue and reduce the risk of tissue damage), or to assist in moving/flowing a biological tissue through the tool. For example, in the hair harvesting procedure, the delivery of a small amount of fluid to the distal end of the cannula may serve to keep any harvested follicular unit moist while it is located in or moves through the harvesting tool. Examples of fluids that may be delivered through the delivery system of the present application include without limitation liquid media which, in reference to medical or cosmetic procedures, is nurturing to biological tissue and/or prevents tissue desiccation (for example, water, standard saline solution, buffered saline solution, and other physiologic fluids). According to one aspect, apparatus, systems and methods for delivery of fluid to the lumen of a needle or cannula are provided that can be used in hair harvesting and/or hair implantation procedures. In yet a further aspect of the invention, the automated delivery of fluid, for example, to clean, flush or lubricate the cannula or a needle may be adapted for a hand-held or manual hair transplantation tool. According to the various embodiments described herein, a variety of systems and methods have been developed which enable fluid to be delivered to the lumen of a tool during an automated medical procedure such as a hair transplantation procedure that are efficient, cost-effective, convenient, substantially automated, and do not require the user to interrupt the medical procedure.

FIG. 1 is a schematic perspective view of an example of a robotic system 100 for harvesting and/or implanting follicular units into a body surface, one example being the scalp of a patient. The system 100 comprises a cart 110 on which a robotic arm 115 is mounted. A tool assembly 120 may be coupled, for example, to the distal end of the robotic arm 115. The tool assembly 120 comprises a tool 125, such as a harvesting tool or implantation tool, with distal end 130. Various motors and other movement devices may be incorporated to enable fine movements of the distal end 130 of the tool 125 in multiple directions. The system 100 may further include at least one image acquisition device (not shown) configured to acquire images of a hair transplantation surface on a patient 150. A computer (also not shown) may instruct the movement of the robotic arm 115 and also various movements of the tool assembly 120. The computer may comprise a processor which may act, for example, through a controller that may be operatively coupled to the robotic arm 115 and configured to control the motion of the robotic arm 115, including the motion based on the images or data acquired by the image acquisition device. The system 100 may further comprise an image processor for processing images obtained from the image acquisition device and providing for motion of the robotic arm 115 based on the images or data acquired by the image acquisition device. The image processor may be a separate device or it may be incorporated as a part of the processor. Alternatively, controller may be incorporated as a part of the processor, so that all processing and controls of all movements of all the tools, the robotic arm and any other moveable parts of the assembly, including those based on the images or data acquired by the image acquisition device, are concentrated in one place. The system 100 may further comprise a monitor, keyboard, mouse, and other tools, devices and components useful in harvesting, and/or implantation of the hair follicles, or in hair treatment planning (also not shown). In addition, the system 100 may comprise an interface which may include hardware ports, cables, leads, and other data transmission means, or it may comprise a computer program.

Typically, the processor operates as a data processing device, for example, it may be incorporated into a computer. The processor may include a central processing unit or parallel processor, and input/output interface, a memory with a program, wherein all the components may be connected by a bus. Further, the computer may include an input device, a display, and may also include one or more secondary storage devices. The bus may be internal to the computer and may include an adapter for receiving a keyboard or input device or may include external connections.

The processor may execute a program that may be configured to include predetermined operations. The processor may access the memory in which may be stored at least one sequence of code instructions comprising the program for performing predetermined operations. The memory and the program may be located within the computer or may be located external thereto. By way of example, and not limitation, a suitable image processor may be a digital processing system which includes one or more processors or other type of device. For example, a processor and/or an image processor may be a controller or any type of personal computer ("PC"). Alternatively, the processor may comprise an Application Specific Integrated Circuit (ASIC) or Field Programmable Gate Array (FPGA). It will be understood by those of ordinary skill in the art that the processor and/or the image processor for use with the present invention is programmed and configured to perform various known image processing techniques, for example, segmentation, edge detection, object recognition and selection. These techniques are generally known and do not need to be separately described here. The methods described herein may be implemented on various general or specific purpose computing systems. In certain embodiments, the methods of the present application may be implemented on a specifically configured personal computer or workstation. In other embodiments, the methods may be implemented on a general-purpose workstation, including one connected to a network. Alternatively or additionally, the methods of the invention may be, at least partially, implemented on a card for a network device or a general-purpose computing device. The processor/image processor may also include memory, storage devices, and other components generally known in the art and, therefore, they do not need to be described in detail here. The image processor could be used in conjunction with various hand-held, partially automated and fully automated (including robotic) hair transplantation systems and devices, including but not limited to systems for hair harvesting, or hair transplantation.

The program that runs the method and system may include a separate program code including a set of instructions for performing a desired operation or may include a plurality of modules that perform such sub-operations of an operation, or may be part of a single module of a larger program providing the operation. The modular construction facilitates adding, deleting, updating and/or amending the modules therein and/ or features within the modules.

The system 100 may incorporate a fluid delivery system 105 according to one aspect of the invention. The fluid delivery system 105 may be semi- or fully-automated. In this particular embodiment, the fluid delivery system 105 is configured to be easily accessible on the cart 110, through a cover 140. The cover 140 may provide a protective barrier to contents therein, and/or provide a port of entry or opening 145 into the fluid delivery system 105. The fluid delivery system 105 is shown in greater detail in FIG. 2.

Figure 2:
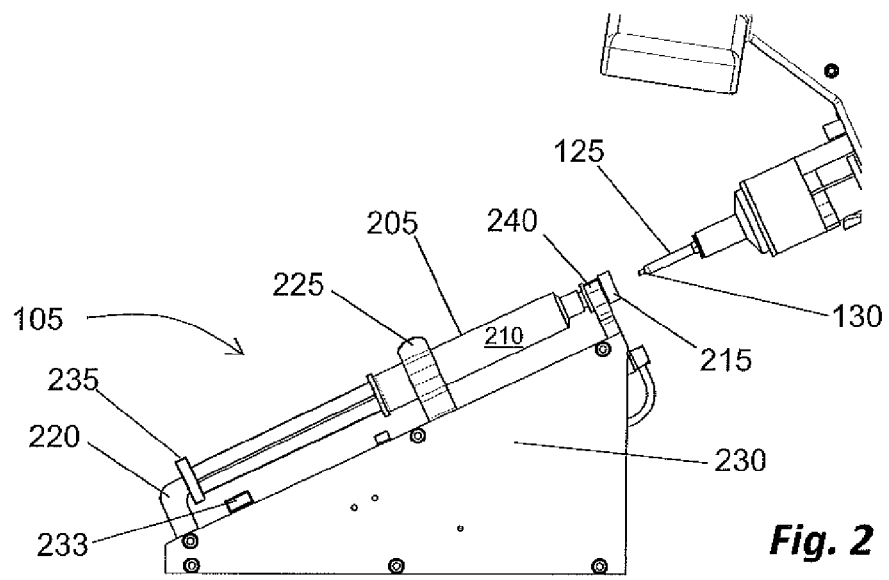
FIG. 2 is an example of a saline delivery system which could be utilized in various embodiments of the invention.

FIG. 2 is a schematic representation of a fluid delivery system 105 according to an aspect of the invention, comprising a fluid dispensing mechanism, illustrated here in the form of a syringe 205 in which the fluid 210 (e.g. saline) is contained, and an adapter 215 for restricting the amount of fluid 210 that is provided to the distal end 130 of the tool 125. An actuation mechanism 220 is configured such that placement of the distal end 130 of the tool 125, for example, within or at the opening 145 (seen in FIG. 1) may actuate the actuation mechanism 220. Fluid 210 is then caused to travel through a pathway (described below) in the adapter 215 such that a restricted and/or controlled flow of fluid 210 moves towards the distal end 130 of the operating tool 125. The syringe 205 is held in place at one end or closer to one end, for example, by a holder or clip 225 which may comprise a spring clip, hence able to accommodate syringes of various sizes, in terms of diameter. The clip 225 may be placed on the bracket 230, which in turn may be affixed to the cart 110, and may accommodate syringes of various sizes, in terms of overall length and/or diameter. At the other end, a second clip 240 may be provided, whose function is to enable accurate location of the tip of the syringe 205. Typically, syringes made by different vendors have different overall lengths and/or diameters, and the only feature that they have in common is a male luer fitting molded at the tip of the syringe. In one embodiment, the second clip 240 is configured to accommodate the adapter 215 and to keep it in a fixed position. In this manner, the tip of the syringe of any size may be accurately positioned for fluid delivery with the aid of the second clip 240. The clip 240 may be also placed on the bracket 230, which in turn may be affixed to the cart 110. In one aspect of the invention, an apparatus including an adapter 215, and one or more clips or holders (e.g. universal holding mechanisms) may be provided as a unit (for example, on a bracket or some base). In some embodiment, it may be movable and positioned by a user at an appropriate location for convenience of operation. In other embodiments, such unit may be permanently fixed, for example, to the cart, or operatively connected inside a cover on the cart (as illustrated in FIG. 1. In some additional embodiments, such unit may be attached to the robotic arm of the automated system. In operation, the plunger 235 of the syringe is fully extended when the syringe is full of fluid 210, and is operably coupled to the actuation mechanism 220. Various sensors may be incorporated into the fluid delivery system 105, including for example an optical sensor 233 to indicate when the end of the plunger 235 comes into proximity to the syringe body, thus indicating that the syringe is no longer full of fluid, and may need re-filling. Signals from the sensor may be fed back into the processor, and utilized to inform the user that the syringe requires attention. The signal may also prevent further actuation of the actuation mechanism so the system does not try to dispense further fluid until the syringe has been re-filled by the user. Additional sensors may be used for detection of the fluid, location of the syringe plunger or other fluid dispensing mechanism, or a proper alignment between the adapter and the distal end of the tool.

Figure 3:
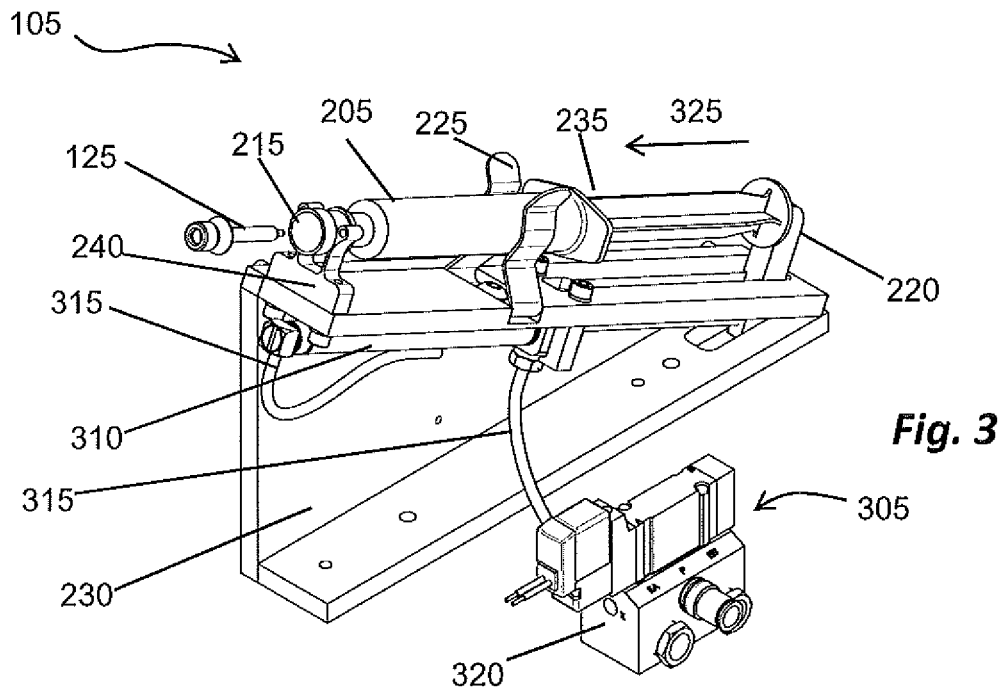
FIG. 3 is the saline delivery system of FIG. 2 as viewed from the opposite side.

FIG. 3 is a schematic representation of the fluid delivery system 105 of FIG. 2, as seen from the opposite side, in which an example of an actuation system 305 can be seen as well. The actuation system 305 may comprise the actuation mechanism 220, a gas cylinder 310 that actuates the syringe plunger 235, various tubing 315, and a gas supply 320. Any or all these aforementioned structures may be housed, for example, on or within the cart 110. In one example, the gas supply comprises a pump which takes in air and controls the air it outputs into the cylinder 310 via an air valve. In operation, the syringe 205 is filled with a fluid such as saline solution (from a petri dish or elsewhere), and placed into the holding structure, such as clips 225 and 240, with the end of the syringe plunger 235 extended and operatively coupled to the actuation mechanism 220. Operatively coupling may merely require that the syringe plunger 235 be disposed adjacent the actuation mechanism 220 and maintain contact therewith. In one example, the actuation system 305 is configured such that when the syringe is full, supplying no air keeps the syringe plunger fully extended, or sufficiently extended such that no fluid 210 is expelled from the syringe 205. However, as the supply of air is increased, and more air is fed to the gas cylinder, pressure is exerted on the actuation mechanism 220, and the actuation mechanism 220 moves in the direction of the arrow 325 as indicated. In turn, movement of the actuation mechanism 220 actuates the syringe plunger 235, causing it to also move in the direction of the arrow 325, and consequently causing some of the fluid in the syringe 205 to be expelled from the syringe. The fluid that is expelled from the syringe 205 enters the adapter 215, which is shown in greater detail in FIGS. 4 and 5 below.

In one embodiment, a control system (not shown) is operatively connected to the gas supply 320 and operates to control the amount of fluid dispensed. The control system may be incorporated into the computer that instructs operation of the robotic arm 115, and/or operation of the tool assembly 120. The fluid dispenser control system may comprise a standard control system as is known in the art to selectively determine the volume of fluid to be dispensed by the fluid dispenser and into the adapter 215. For example, the fluid dispenser control system may operate the gas supply to provide a gas at a predetermined pressure for a predetermined time, and repeat or cycle its operation a predetermined number of times. For example, the pump may supply a pressure sufficient to dispense fluid from the syringe 215, which may be as low as 0.1 psi, and range as high as needed to achieve the intended effect, depending upon the fluid flow rate sought, though a pressure in the range of approximately 20 to 50 psi, for example 40 psi, would be a reasonable pressure. In some embodiments a pulse of three small droplets may be created, for example, by activation of pressure, as mentioned above, three times over a ten second cycle. In this manner, with an aperture of a known diameter, a known number of drops (for example, two), a known amount of fluid (for example, no more than 5 c.c.), or a designed fluid flow rate can be made to dispense out of the syringe 205, and into the adapter 215. The control of volume of fluid dispensed by the fluid dispenser in a clinical setting may, for example, be adjusted taking into consideration the variability of biologic fluid (blood, lymph, serous fluid) in the field and the degree of lubrication required for tool dissection given tissue variability (for example, a longer duration of dissection may require more lubrication).

Figure 4:
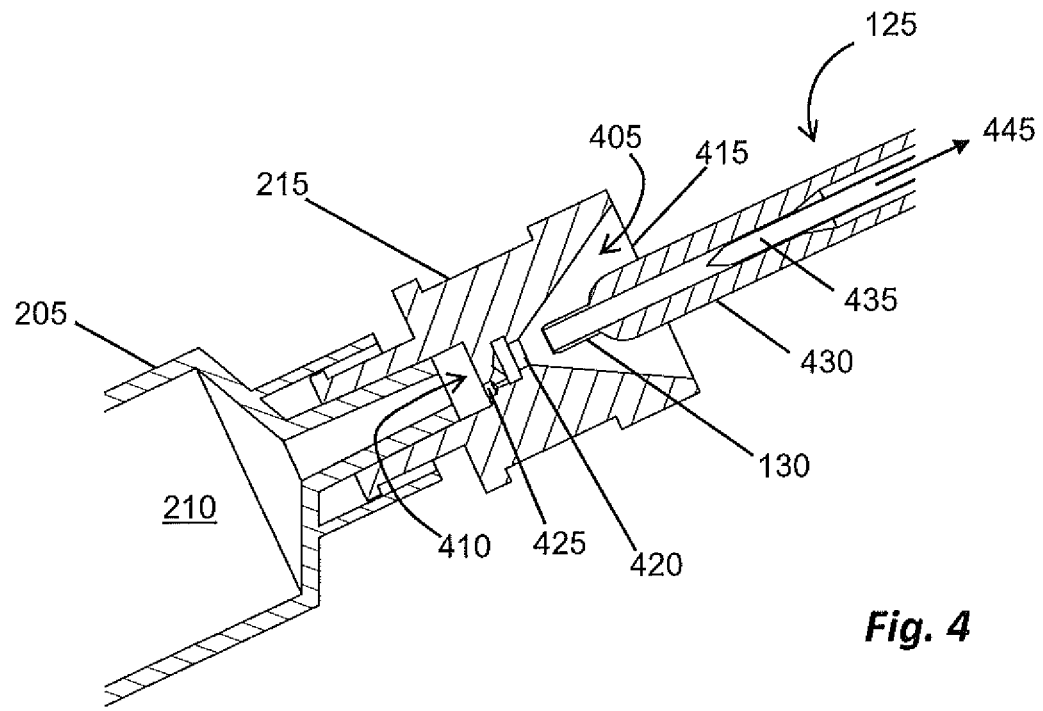
FIG. 4 is a cross-sectional view of the saline delivery system shown by example in FIGS. 2 and 3.

FIG. 4 shows a cross-section of an example of the adapter 215, one end of which is attached to a syringe 205, and the other end has a tool 125 (e.g. a cannula or a punch) with a distal end 130 disposed within it. The adapter 215 comprises a first opening 405 and a second opening 410. In one embodiment, the first opening 405 is configured such that it forms the port of entry or opening 145, and is located on the cover 140 of the cart 110 (seen in FIG. 1). The first opening 405 comprises two ends, a first end 415 configured to receive a distal end 130 of a tool 125, and a second end which is configured with an aperture 420 therein, to receive fluid from the second opening 410. In one example, the first opening 405 may be tapered to facilitate placement of the tool 125 within the opening, though tapering is not required. In another example the first opening may be configured such that the distal end 130 of the tool 125 slidably fits within the first opening 405.

The aperture 420 in the second end of the opening 405 is configured to provide access to the second opening 410, providing the entrance to a pathway such that fluid expelled from the syringe 205 and moving in the direction of the tool 125, travels along the pathway and towards the tool 125 through the aperture 420. The proximal end of the tool 125 may be operatively in communication with a pressure differential or vacuum source 445, such that the lumen of the tool 125 is in communication with the pressure differential supply 445. The second end 420 is also configured such that it is sized to accommodate the distal end 130 of the cannula 125.

The second opening 410 is configured to facilitate coupling (direct or indirect) to the syringe 205 to receive fluid 210 from the fluid dispenser. Both the internal and the external dimensions of the second opening 410 are sized and configured such that they closely fit and mechanically engage and contact the walls of the syringe 205. In this particular instance, it can be seen that the coupling facilitates the connection via means of a luer taper connection, thus accommodating substantially all commercially available syringes. The luer taper connection may be a threaded connection enabling the adapter to be screwed securely to the syringe, or be un-threaded and dimensioned to allow the adapter to be pressed together with the syringe, and the two parts being held together by friction.

Figure 5A:
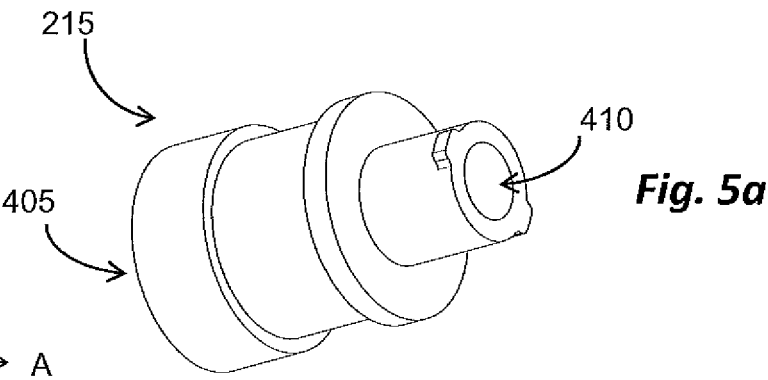
FIGS. 5(a)-(d) show an example of a fluid delivery adapter that may be implemented in an embodiment of the invention.
Figure 5B:
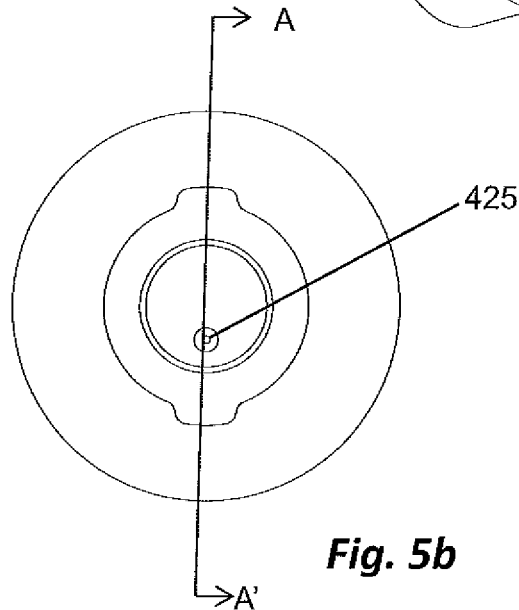
Figure 5C:
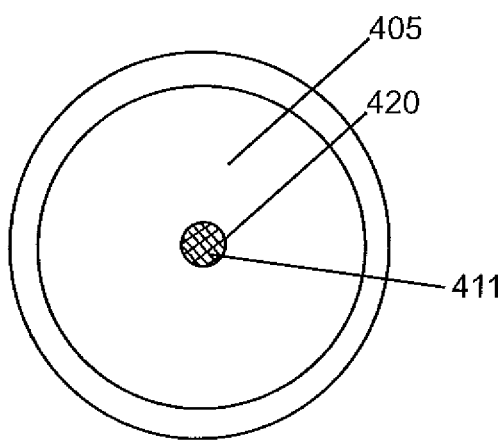
Figure 5D:
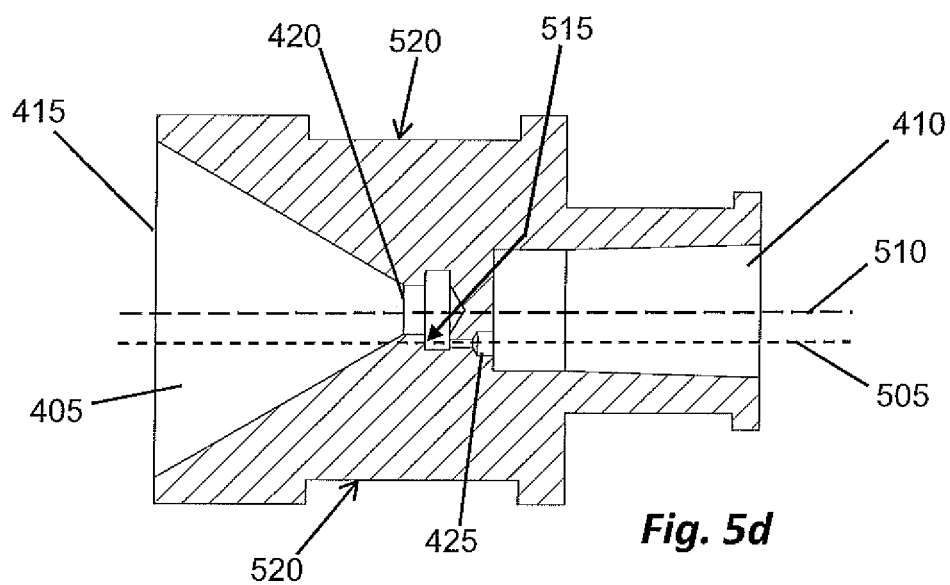

FIGS. 5(a)-(d) illustrate the adapter 215 alone, without the fluid dispenser or syringe 205 attached or the tool (e.g. needle, punch, cannula) 125 disposed within. FIG. 5(a) is a perspective view of the adapter 215, FIG. 5(b) is a view taken from looking into the second end 410, FIG. 5(c) is a view taken from looking into the first end 405 and FIG. 5(d) is a section taken along AA' of FIG. 5(b). From these figures it can be seen that in the illustrated embodiment the first opening 405 is larger than the second opening 410. Also, FIG. 5d shows an example of an embodiment comprising a recessed region or groove 520 that may be configured and sized to accommodate the second clip 240 (shown in FIG. 3).

Figure 6:
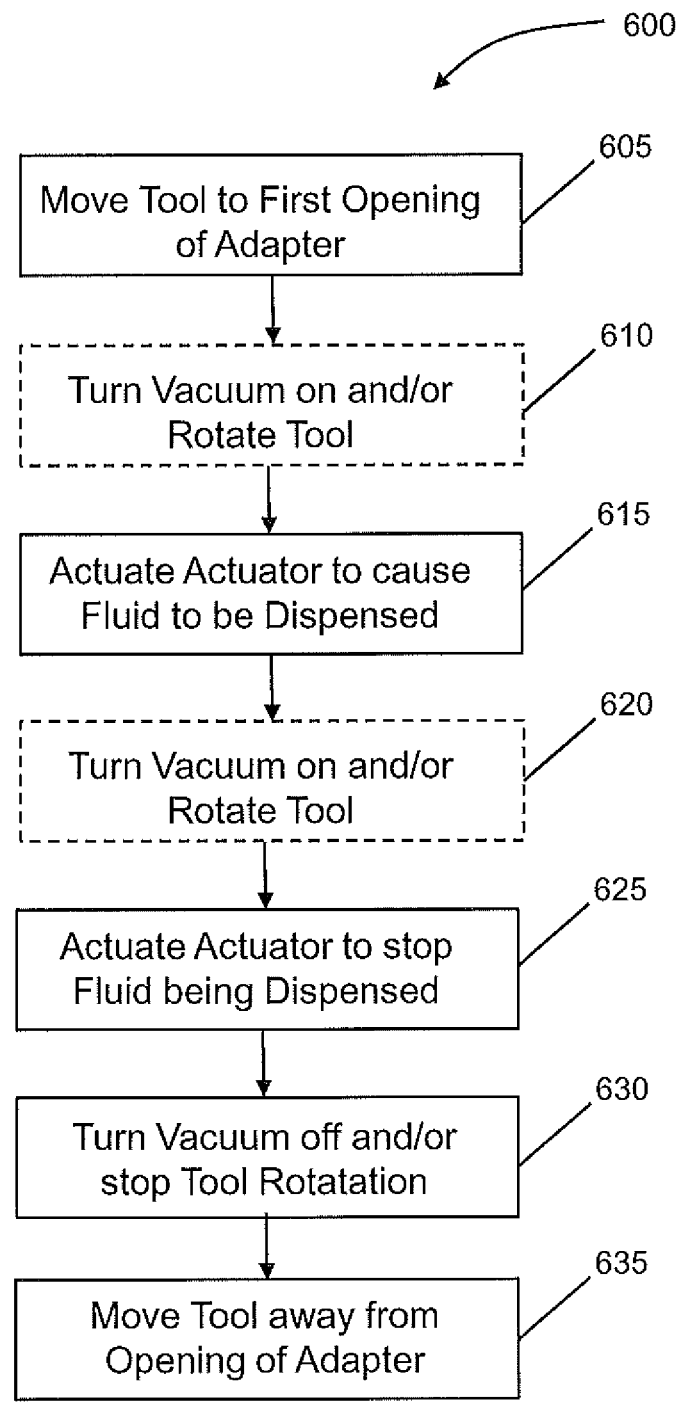
FIG. 6 is a block diagram illustrating a general methodology of an example of an embodiment according to one aspect of the invention.

FIG. 6 is a block diagram illustrating an example of a general methodology 600 employed according to one aspect of the automated fluid delivery of the inventions described herein. At step 605 the tool 125 is moved to the first opening 405 of the adapter 215. In one embodiment where a robotic system is used, the computer can be programmed such that the robotic arm 115 automatically moves the distal end 130 of the tool 125 to the first opening 405 of the adapter 215. For example, in various embodiments the computer may be programmed to cause the tool to move to the opening 405 after the harvesting operation has been carried out for a predetermined time interval, after a row of follicular unit harvests has been completed, after each or a predetermined number of follicular units have been harvested, or at the operator's request, entered through an appropriate interface. The distal end 130 is maneuvered or extended such that it is within or at the first opening 405. In those embodiments where a handheld tool is used, a user may move the tool to the first opening of the adapter. In some embodiments, especially those fully automated, various sensors may be used, for example, to ascertain that the tool is properly connected or aligned with the first opening of the adapter, or that the adapter is present and in a working mode. In an optional step 610, the vacuum may be turned on. In some embodiments, an image acquisition device may be disposed on the robotic arm and able to identify at least the outline of the end of the adapter 215. It will be understood by those of ordinary skill in the art that the processor for use with the present invention is may be programmed and configured to perform various known image processing techniques, for example edge detection, objection recognition and selection. These techniques are generally known and do not need to be separately described herein. On identification of the adapter 215, and having ascertained the distance from the robotic arm and/or the tool 125 to the adapter 215 (also using known processing techniques), should the end of the adapter 215 be found to be within a predetermined range, the processor may cause the vacuum to be turned on. In other embodiments, when the distal end 130 is maneuvered within the first opening 405, a sensor may sense the cannuala's presence and send appropriate instructions via electronic or other such means to turn the vacuum on. In certain embodiments and applications to achieve more efficient cleaning, flushing or lubricating, optionally, the tool 125 may be caused to rotate, for example, using a processor, or a sensor in a manner similar to that described in relation to turning the vacuum on.

In step 615, the actuator may be actuated, for example, under computer control to cause fluid to be dispensed from the syringe. The gas supply 320 may be operated to supply a predetermined volume of gas through the tubing 315 and gas cylinder 310 thereby operating to move the actuator mechanism 220 in a direction such that the syringe plunger forces fluid 210 from the syringe 205 and out into the adapter 215. As mentioned beforehand, in some embodiments this operation may be cyclic or repeated a number of times to provide the desired amount of fluid and/or the desired fluid flow rate. For example, when an embodiment of the adapter such as one shown in FIG. 4 is used, as the fluid 210 enters the second opening 410 of the adapter 215, it travels through the aperture 425 and along the pathway emerging through aperture 420 at the second end of the first opening 405 of adapter 215. As illustrated in FIG. 5(d), the pathway from the aperture 425 to the aperture 420 may be such that the longitudinal axis 505 that extends through the aperture 425 is offset from the longitudinal axis 510 that extends through the aperture 420. In other words, the pathway may comprise at least two portions that are axially off-set. In addition, as fluid 210 initially propagates through aperture 425 it encounters a physical obstacle or boundary 515, which in this particular example is a wall 515 that is substantially orthogonal to the fluid's initial direction of propagation. In this manner, the fluid does not directly pass through the adapter 215 via apertures 425 and 420 and it is not squirted out at full pressure from the first opening of the adapter 215. Instead, the fluid may build up, and for example, form a drop that will be delivered at the first opening of the adaptor and to the tool 125 positioned at the first opening.

It will be appreciated that the provision of offset axes as described above is only one example of ways in which the fluid delivery can be restricted, other methods to restrict fluid flow will be apparent to those skilled in the art. For example, in another embodiment, the adapter 215 may be configured with one common axis, but may incorporate a barrier 411 along the passway between the first and the second openings of the adapter. Such barrier 411 may take various forms and configurations, for example, it may comprise a perforated wall, or a plate having plurality of smaller apertures or ports. The barrier may be configured such that the fluid flow is at least partially restricted, or gradually accumulates on one side of the barrier before it is able to pass in a slow and controlled manner to the other side.

As the small quantity of fluid (which may be a few drops per second) enters the second end of the first opening 405, it accumulates there as mentioned above, and consequently the distal end 130 of the cannula 125 may find itself disposed within a collection of fluid. In some embodiments, the distal end 130 may be cleaned of any blood, tissue or other such debris that may be on its surfaces. The vacuum source that was activated creates a suction force and causes an airflow through the lumen of the cannula 125. The airflow pulls any residual fluid at the second end of the adapter 215, in the vicinity of the aperture 420 up and into the lumen such that the fluid contacts its inner surfaces. In this manner the inner surfaces of the lumen are flushed of any blood, tissue or other such debris that may be on their surfaces. Also, it may serve to lubricate the tool and/or any follicular unit that may be contained in the lumen of the tool. Furthermore, provision of fluid may aid in keeping the harvested follicular unit moist for subsequent implantation, or aid the follicular unit in its travel to its destination. In the present example, once the residual fluid is removed from the cannula 125, it will flow along the moving airstream in the proximal direction. In the event that step 610 was not implemented earlier, it may be implemented as an optional step 620, thus enabling the cannula to be flushed as described hereinbefore.

A system according to an embodiment of the current invention may be utilized with any tool 125. For example, a single sharp punch or needle, or tool comprising two concentric needles or punches, such as the double cannula configuration described in U.S. Patent Publication No. 2008/0234699, which is hereby incorporated herein by reference. FIG. 4 illustrates such a double cannula configuration comprising, for example, a punch 435 responsible for punching or making of the harvesting site and a blunt cannula 430 responsible for dissection of the follicular unit from the surrounding tissue. As illustrated, in the process of cleaning of such a double cannula configuration, the inner cannula 435 may be retracted into the outer cannula 430 (as will be explained in greater detail below). Alternatively, cleaning of such a cannula configuration may be carried out with the inner cannula extending from the end of the outer cannula. If the tool comprises two needles or cannulas, as mentioned above, the lumen of either or both of such needles may be operatively in communication with a pressure differential or vacuum source 445. In the example of FIG. 4, the lumen of the inner cannula 435 is shown to be in communication with the pressure differential supply 445.

Having delivered the desired amount of fluid to the tool, in step 625 the actuator is caused to stop fluid from being dispensed from the syringe, and after allowing a few more seconds for residual fluid in the vicinity of the aperture 420 to be pulled via the vacuum, in step 630 the vacuum is turned off. In those embodiments where the tool was rotated, such rotation may be also stopped before the tool is moved away from the adapter 215 in step 635.

According to the methods described in reference to FIG. 6, step 605 comprised moving the tool to the opening in the adapter and step 635 comprised moving the tool away from opening of adapter. However, in certain embodiments and applications these steps may not be needed. For example, in alternative configurations where automated system (e.g. robotic system) is used, a fluid dispensing apparatus may be attached or mounted, for example, on the tool assembly 120, and actuation of the actuation mechanism does not require that the distal of the tool be placed at the first opening of the adapter. Instead, the fluid may be delivered from the fluid dispenser, such as syringe 205, through the adapter and via additional tubing (not shown) to the distal end 130 of the tool 125. The adapter and its operation, as well as general concepts described in reference to FIGS. 2-5 may be adjusted and used accordingly accommodate an embodiment where a distal end of the tool is not placed within or at the first opening of the adapter. Similarly, it will be understood by those of ordinary skill in the art that the methodology described in reference to FIG. 6 will be adjusted accordingly for such configuration.

For example, in one embodiment, the computer may be programmed to actuate an actuation mechanism 220 such that fluid is automatically dispensed from a syringe 205 after the harvesting operation has been carried out for a predetermined time interval. In other embodiments the computer may be programmed to actuate an actuation mechanism after a row of follicular unit harvests has been completed, or after each or a predetermined number of follicular units have been harvested, or at the operator's request (for example, entered through an appropriate interface). The computer may also be programmed to activate a pressure or vacuum source to create a suction force and cause an airflow through the lumen of the tool 125. Dispensed fluid would enter the second opening 410 of the adapter 215, with its flaw restricted as it travels towards the first opening 405. On arrival at the first opening 405, the restricted flow of fluid may pass, for example, into one end of the tubing and through the tubing to its other end, which may be disposed near or at the distal end, or within a certain distance from the distal end 130 of the tool 125. The fluid delivered to the tool 125 would be pulled by the created airflow into the lumen and serve to flush the lumen. It will be apparent to the user that it may be desirable to ensure that the distal end 130 of the tool 125 is not inserted into the body surface of the patient when the tool is flushed, and the computer may be programmed appropriately to ensure the removal of the tool from the patient prior to actuating the actuation mechanism 220 or activating the vacuum source.

According to one aspect, various methods of automatically dispensing fluid are provided. Some of these methods may be implemented with the hand-held devices, some of the methods may be implemented using at least partially automated, including robotic, systems. For example, some method may comprise using a unique adapter apparatus disclosed in the present application.

With reference to various methods described herein, it will be apparent that the number of steps that are utilized for such methods are not limited to those described. Also, the methods do not require that all the described steps are present. Although the methodology described above as discrete steps, one or more steps may be added, combined or even deleted, without departing from the intended functionality of the embodiments of the invention. The steps can be performed in a different order or have the steps shared between more than one processor, for example. It will also be apparent that the method described above may be implemented using manual, partially or substantially automated systems, including using robotic systems.

According to another aspect, a robotic hair transplantation system is provided, the system including a robotic arm with a hair transplantation tool attached thereto. In one embodiment, the robotic system is situated on a cart, and the cart is configured to also accommodate a fluid dispensing apparatus or system. In another embodiment, the fluid dispensing apparatus may be positioned on the robotic arm, or the tool assembly, or other appropriate location. Such fluid dispensing apparatus may comprise a fluid dispensing adapter of the present application. The robotic system may be configured to move the robotic arm and/or the hair transplantation tool, such that a distal end of the tool is substantially aligned with the first opening of the fluid dispensing adapter. When the distal end of the tool is so aligned, an actuation mechanism actuates fluid delivery through the fluid dispensing adapter to the hair transplantation tool.

According to another aspect, a fluid dispensing apparatus is provided. The fluid dispensing apparatus may comprise a fluid dispensing adapter and an actuation mechanism. The fluid dispensing adapter may comprise two openings, a first opening to receive a tool, such as a hair harvesting or hair implantation tool, and a second opening to receive fluid from a fluid dispenser, and it may be configured to provide controlled delivery of a small volume of fluid. A fluid dispenser may be provided and sold separately, and in some embodiments, the fluid dispensing adapter is universal and could be implemented with various fluid dispensers, such as syringes. In some embodiments, fluid may be delivered through the fluid dispensing adapter to a distal end of a cannula, needle, punch or other appropriate tool.

While the invention has been described in its preferred embodiments, the words which have been used are words of description and not of limitation. These embodiments are susceptible to various modifications and alternative forms, and it should be understood that the invention generally, as well as the specific embodiments described herein, cover all modifications, equivalents and alternatives falling within the scope of the appended claims. In one variation of the invention, a manual or hand-held hair harvesting tool may be utilized, and the user may temporarily terminate harvesting to lubricate or clean, for example, a hand-held harvesting tool. In this embodiment the user would move the cannula to the first opening of the adapter, which may be housed in a stand-alone cleaning unit, along with associated elements described above. Having done so, the presence of the distal end of the cannula would initiate the fluid dispensing process through an adapter apparatus of the present application. The user ensures that the distal end of the cannula remained in the adapter for a sufficient time to enable the lubrication or cleaning process to be completed, or the system may be configured such that removal of the distal end of the cannula from the first opening of the adapter would prevent further fluid from being dispensed. By way of non-limiting example, it will be appreciated by those skilled in the art that particular features or characteristics described in reference to one figure or embodiment may be combined as suitable with features or characteristics described in another figure or embodiment. Further, those skilled in the art will recognize that the devices, systems, and methods disclosed herein are not limited to one field, such as hair restoration, but may be applied to any number of fields. Therefore, changes may be made within the appended claims without departing from the true scope of the invention. Applicant regards the subject matter of the invention to include all novel and nonobvious combinations and subcombinations of the various elements, features, functions, and/or properties disclosed herein.

What is claimed is:

1. An apparatus for dispensing fluid, the apparatus comprising:
    an adapter configured to restrict a volume of fluid provided to a tool, the adapter including:
        a first opening configured to receive a distal end of the tool;
        a second opening configured to receive fluid from a fluid dispenser, and
        a pathway disposed between the first opening and the second opening, the pathway configured to restrict a flow of fluid from the second opening to the first opening;
    an actuation mechanism configured to cause fluid to be dispensed from the fluid dispenser to the second opening of the adapter when the distal end of the tool is disposed within or at the first opening of the adapter; and
    one or more sensors configured to detect 1) whether the fluid dispenser is no longer full of fluid, and/or 2) alignment between the distal end of the tool and the adapter.

2. The apparatus of claim 1, further comprising a fluid dispenser, the fluid dispenser including a syringe having a plunger, and wherein the actuation mechanism actuates the syringe plunger.

3. The apparatus of claim 2, further comprising a sensor configured to indicate a location of the plunger, and/or if less than a predetermined amount of fluid is disposed within the syringe.

4. The apparatus of claim 2, wherein the second opening is sized and configured to engage and contact walls of the syringe.

5. The apparatus of claim 1, wherein the actuation mechanism is actuated by a pressure differential to cause fluid flow.

6. The apparatus of claim 1 further comprising a holder configured to accommodate fluid dispensers of various length and diameters.

7. The apparatus of claim 6, wherein the holder is a spring clip.

8. The apparatus of claim 1, wherein the pathway comprises at least two axially off-set portions.

9. The apparatus of claim 1, wherein the pathway comprises a barrier configured to restrict a flow of fluid between the first opening and the second opening of the adapter.

10. The apparatus of claim 9, wherein the barrier comprises a perforated wall.

11. The apparatus of claim 1, wherein the apparatus is operatively attached to a cart of a robotic system, the robotic system further comprising a robotic arm, a tool mounted on the robotic arm and a processor configured to position a distal end of the tool within or at the first opening of the adapter.

12. The system of claim 11, wherein the robotic system is a hair transplantation system, and the tool is a hair harvesting or a hair implanting tool.

13. The apparatus of claim 12, wherein the actuation mechanism is configured to cause automatic fluid delivery after:
    a harvesting operation has been performed for a predetermined time interval, or
    a row of follicular unit harvests has been completed, or
    each or a predetermined number of harvests, or
    at a user's request.

14. The apparatus of claim 11, wherein the apparatus is configured to be easily accessible on the cart, through a cover, the cover providing a protective barrier to the apparatus and a port of entry into the first opening.

15. The apparatus of claim 1, further comprising a computer configured to control actuation of the actuation mechanism to control fluid delivery.

16. The apparatus of claim 1, further comprising a control system configured to control the amount of fluid to be delivered into the adapter.

17. The apparatus of claim 16, wherein the control system is adjustable to control the volume of fluid dispensed based on one or more of at least the type of fluid, the degree of lubrication required, a designed fluid flow rate, a known amount of fluid to be dispensed, or the number of drops of fluid to be dispensed.

18. The apparatus of claim 1, wherein the first opening is tapered to facilitate placement of the distal end of the tool within the first opening.

19. The apparatus of claim 1, wherein the tool comprising a lumen, and the apparatus further comprises a pressure differential source configured to cause an airflow through the adapter and the lumen of the tool.

20. An apparatus for dispensing fluid, the apparatus comprising:

an adapter configured to restrict a volume of fluid provided to a tool, the adapter including:
- a first opening configured to receive a distal end of the tool,
- a second opening configured to receive fluid from a fluid dispenser, and
- a pathway disposed between the first opening and the second opening, the pathway configured to restrict a flow of fluid from the second opening to the first opening;

an actuation mechanism configured to cause fluid delivery to the second opening of the adapter when the distal end of the tool is disposed within or at the first opening of the adapter;

the fluid dispenser, the fluid dispenser including a syringe having a body and a plunger, and wherein the actuation mechanism actuates the syringe plunger; and a sensor configured to determine a location of the plunger with respect to the syringe body, and/or if less than a predetermined amount of fluid is disposed within the syringe, wherein determination of the location of the plunger in close proximity to the syringe body and/or if less than a predetermined amount of fluid is disposed within the syringe causes the actuation mechanism to be prevented from further actuating, such that the apparatus does not dispense further fluid until the syringe has been re-filled by the user and/or until a greater than a predetermined amount of fluid is disposed within the syringe.

21. The apparatus of claim 20, wherein the pathway comprises at least two axially off set portions.

22. The apparatus of claim 20, wherein the pathway comprises a barrier configured to restrict a flow of fluid between the first opening and the second opening of the adapter.

23. An apparatus for dispensing fluid, the apparatus comprising:
an adapter configured to restrict a volume of fluid provided to a tool, the adapter including:
- a first opening configured to dispense fluid to the distal end of the tool;
- a second opening configured to receive fluid from a fluid dispenser, and
- a pathway disposed between the first opening and the second opening, the pathway configured to restrict a flow of fluid from the second opening to the first opening;

an actuation mechanism configured to cause fluid to be dispensed from the fluid dispenser to the second opening of the adapter; and a processor configured to actuate the actuation mechanism to cause fluid to be dispensed based on one or more of the following: 1) positioning of the tool at a predetermined distance from, or at, or within the adapter, 2) after the tool has performed one or a predetermined number of operations, 3) after a predetermined time, or 4) at a user's request.

24. The apparatus of claim 23, wherein the tool is operatively connected to the first opening of the adapter through a tubing or a connector.

25. The apparatus of claim 23, further comprising an image acquisition device and an image processor configured to determine whether the tool is within a predetermined distance from, at, or within the adapter.

* * * * *